United States Patent [19]

Plummer

[11] Patent Number: 4,513,163

[45] Date of Patent: Apr. 23, 1985

[54] CONVERSION OF AROMATICS TO ISO-PARAFFINS USING A NaAlCL$_4$/HAlCL$_4$ MOLTEN SALT CATALYST SYSTEM

[75] Inventor: Mark A. Plummer, Littleton, Colo.

[73] Assignee: Marathon Oil Company, Findlay, Ohio

[21] Appl. No.: 567,194

[22] Filed: Dec. 30, 1983

[51] Int. Cl.$^3$ .............................................. C07C 5/27
[52] U.S. Cl. ............................. 585/700; 585/940; 585/741; 585/752
[58] Field of Search ............. 585/741, 742, 940, 700, 585/752

[56] References Cited

U.S. PATENT DOCUMENTS

| | | | |
|---|---|---|---|
| 1,825,294 | 9/1931 | Wolcott | 208/117 |
| 2,394,898 | 2/1946 | Cheney et al. | 585/742 |
| 2,408,941 | 10/1946 | Mavity et al. | 585/741 |
| 2,464,201 | 3/1949 | Latchum | 585/741 |
| 2,475,358 | 7/1949 | Moore et al. | 585/741 |

Primary Examiner—Delbert E. Gantz
Assistant Examiner—O. Chaudhuri
Attorney, Agent, or Firm—Jack L. Hummel; Rodney F. Brown

[57] ABSTRACT

The present invention provides a process for producing iso-paraffins from aromatic hydrocarbons comprising contacting the aromatic hydrocarbon or aromatic hydrocarbon-containing feed with a molten salt system comprising sodium tetrachloroaluminate (NaAlCl$_4$) and up to about 25 weight percent hydrogen tetrachloroaluminate (HAlCl$_4$) at a temperature above about 155° C., i.e. that required to maintain the molten state of said mixture, whereby the ring structure is opened and the aromatic compound is rearranged to an iso-paraffin of the same or substantially the same molecular weight.

14 Claims, No Drawings

CONVERSION OF AROMATICS TO ISO-PARAFFINS USING A NaALCL₄/HALCL₄ MOLTEN SALT CATALYST SYSTEM

FIELD OF THE INVENTION

This invention relates to processes for the conversion of aromatic hydrocarbons to iso-paraffins and, in particular, to the use of molten sodium tetrachloroaluminate and hydrogen tetrachloroaluminate to catalyze the conversion reaction.

BRIEF DESCRIPTION OF THE PRIOR ART

The use of molten salts as a medium for organic reactions is well known. For many types of reactions, advantages such as short reaction times, facility of product recovery and improved yields may be achieved. Aluminum chloride ($AlCl_3$) and sodium tetrachloroaluminate ($NaAlCl_4$) systems are among the molten salts frequently used. Use of molten $NaAlCl_4$ is generally known for many Friedal-Crafts catalyzed reactions, e.g. condensation-addition reactions, dehydrogenation-condensation reactions. However, heretofore $NaAlCl_4$ and $AlCl_3$ systems have not been effective in opening aromatic structures.

Aluminum chloride and other metal chlorides, i.e. Friedal-Crafts catalysts, are known to catalyze a number of reactions including rearrangement reactions. By rearrangement reactions is meant those wherein a molecular structure is converted to another with the same or substantially the same molecular weight, e.g. isomerization reactions. In some instances the Friedal-Crafts catalysts require promoters, e.g. $H_2O$ or HCl. However, such metal chloride catalysts, with or without promoters, have not previously been recognized as useful for the rearrangement of aromatics into iso-paraffins. Because of the stability of the aromatic rings structures, most catalysts, including the Friedal-Crafts and known cracking catalysts, are useful simply for cleaving radicals attached to the aromatic ring without opening the ring structure itself.

The $AlCl_3$-HCl co-catalyst system has been used for the alkylation of aromatics with alkenes. However, no opening of the ring structure to form iso-paraffins is involved.

Accordingly, it is an object of this invention to provide a process whereby conversion of aromatics to iso-paraffins is effected in a molten salt medium.

Another object is to provide a co-catalyst system which enhances conversion of aromatics to iso-paraffins.

SUMMARY OF THE INVENTION

The present invention provides a process for producing iso-paraffins from aromatic hydrocarbons comprising contacting the aromatic hydrocarbon or aromatic hydrocarbon-containing feed with a molten salt system comprising sodium tetrachloroaluminate ($NaAlCl_4$) and up to about 25 weight percent hydrogen tetrachloroaluminate ($HAlCl_4$) at a temperature above about 155° C., i.e. that required to maintain the molten state of said mixture, whereby the ring structure is opened and the aromatic compound is rearranged to an iso-paraffin of the same or substantially the same molecular weight.

DETAILED DESCRIPTION OF THE INVENTION

Aromatics useful for practice of the present invention can be virtually any unsaturated ring compound. The aromatics may be single, di- and/or tricyclic alkyl aromatics, such as those represented by the following formulas:

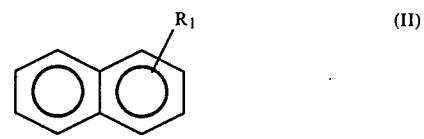

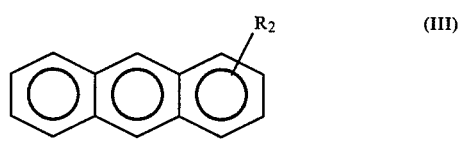

wherein R, $R_1$, and $R_2$ each represent one or more radicals, typically alkyl radicals, of from 1-10 carbon atoms, substituted on the ring structure. Aromatics, substituted or unsubstituted, mixtures thereof and/or feeds-containing such aromatics or mixtures thereof may be treated according to the present invention. In addition to the types of aromatics depicted by formulas I, II and III, compounds containing at least one unsaturated ring and one or more saturated rings may likewise be treated, but as will be known and understood by those skilled in the art, processing according to the present invention is for purposes of opening the unsaturated ring. As with the compounds of formulas I, II and III, each may be unsubstituted or substituted with one or more radicals. Also, among the aromatic-containing feeds useful for practice of the present invention are typical petroleum oils and/or refinery products.

The catalyst of the present invention is a molten salt system comprising $NaAlCl_4$ and up to 25 weight percent $HAlCl_4$. Typically, the ratio of $NaAlCl_4$ to $HAlCl_4$ will be greater than 3 to 1.

The $NaAlCl_4$ molten salt portion of the catalyst system useful in the practice of the present invention comprises a mixture of aluminum chloride ($AlCl_3$) and sodium chloride (NaCl) on about a one to one molar basis and is manufactured at about 155° C. to about 225° C. with reaction times of about 5 to about 30 minutes. In some instances the $NaAlCl_4$ is made by using a ratio of $AlCl_3$ to NaCl slightly greater than one to one, i.e., that there be about 1 to 10 mole percent excess of $AlCl_3$, in order to assure complete conversion of NaCl to $NaAlCl_4$. In these instances, after formation of $NaAlCl_4$ substantially all of the excess $AlCl_3$ is vaporized leaving the basic 1:1 molar ratio.

By way of example, $NaAlCl_4$ is prepared by mixing $AlCl_3$ and NaCl in an initial 1.02 to 1.00 mole ratio, respectively, for about 12–15 minutes at a temperature of about 185°–205° C. and a pressure of 0.82 atmospheres (82.9 kPa). The batch reaction can be terminated when all the excess $AlCl_3$ has vaporized from the molten catalyst.

Where $NaAlCl_4$ is prepared separately the co-catalyst system may advantageously be prepared by the addition of $AlCl_3$ and gaseous HCl to the $NaAlCl_4$. Typically, $AlCl_3$ in an amount comprising from about 0.4 to about 20.0 weight percent of the $AlCl_3$-$NaAlCl_4$ mixture is added thereto under a gaseous HCl pressure of from about 0.8 to about 50.0 atmospheres (81 to 5066 kPa), at temperatures of from about 155° C. to about 350° C., and reaction times of about 0.1 to about 2.0 hours. Preferably, the final $HAlCl_4$ content in the $NaAlCl_4$/$HAlCl_4$ co-catalyst is from about 0.5 to about 25.0 weight percent. More preferably the $HAlCl_4$ content of the final co-catalyst is about 1.0 to about 15.0 weight percent, and most preferably is about 1.5 to about 10.0 weight percent.

The process for converting aromatics to iso-paraffins is most advantageously operated at pressures from about 0.8 to about 140 atmospheres (about 81 to about 14185 kPa), preferably from about 7 to about 70 atmospheres (about 709 to about 7093 kPa). The reaction temperature at which the aromatic feed and molten $NaAlCl_4$/$HAlCl_4$ co-catalyst are contacted is above 155° C., and preferably from about 200° C. to about 550° C. and more preferably from about 300° C. to about 450° C. The contacting or residence time of the feed aromatic hydrocarbon is from about 0.25 to about 4.0 hr. (lb. catalyst per lb. of aromatic feed per hr.).

Practice of the present invention results in rearrangement of the unsaturated aromatic hydrocarbon ring-containing compounds to iso-paraffins of identical or substantially identical molecular weight. This as opposed to previously known reactions using the same or similar catalysts wherein radicals are cleaved or the starting compound is in some other way reformed into lower molecular weight products. By iso-paraffins is meant branched chain hydrocarbons having at least one tertiary carbon atom, i.e. at least one carbon atom bonded to three other carbon atoms. In some instances, e.g. where the feed is a mixture of aromatics and/or aromatics and other non-aromatic hydrocarbons, practice of the present invention will result in an increase in iso-paraffin products.

What is claimed is:

1. A process for producing iso-paraffins from aromatic hydrocarbons comprising contacting said aromatic hydrocarbons with a molten mixture comprising $NaAlCl_4$ and from about 0.5 to about 25 weight percent $HAlCl_4$ at a temperature sufficient to maintain the molten state of said mixture.

2. A process according to claim 1 wherein said contacting is at a temperature above about 155° C.

3. A process according to claim 2 wherein the temperature is from about 200° to about 550° C.

4. A process according to claim 3 wherein the temperature is from about 300° to about 450° C.

5. A process according to claim 1 wherein said contacting is at a pressure of from about 0.8 to about 140 atmospheres.

6. A process according to claim 5 wherein said contacting is at a pressure of from about 7 to about 70 atmospheres.

7. A process according to claim 1 wherein the $HAlCl_4$ content of said molten mixture is from about 1.0 to about 15.0 weight percent.

8. A process according to claim 1 wherein said contact is from about 0.25 to about 4.0 hours.

9. A process for producing an iso-paraffin compound from an aromatic hydrocarbon compound comprising contacting said aromatic compound with a molten mixture comprising $NaAlCl_4$ and $HAlCl_4$ in a ratio greater than about 3 to 1 and at a temperature sufficient to maintain the molten state of said mixture.

10. A process according to claim 9 wherein said contacting is at a temperature above about 155° C.

11. A process according to claim 10 wherein said contacting is at a temperature from about 200° to about 550° C.

12. A process according to claim 9 wherein said contacting is at a pressure of from about 0.8 to 140 atmospheres.

13. A process according to claim 9 wherein said contacting is for a time period of about 0.25 to about 4.0 hours.

14. A process for producing an iso-paraffin hydrocarbon from an aromatic hydrocarbon comprising contacting said aromatic hydrocarbon with a molten salt mixture comprising $NaAlCl_4$ and from about 0.5 to about 25 weight percent $HAlCl_4$ at a temperature above about 155° C. and a pressure above about 0.8 atmospheres and for a time of about 0.25 to about 4.0 hours.

* * * * *